US006664076B2

(12) United States Patent
Green et al.

(10) Patent No.: US 6,664,076 B2
(45) Date of Patent: Dec. 16, 2003

(54) MODIFICATION OF BACTERIA

(75) Inventors: Edward M. Green, Surrey (GB); Fiona S. Cusdin, Surrey (GB); Namdar Baghaei-Yazdi, London (GB); Muhammad Javed, Essex (GB)

(73) Assignee: Elsworth Biotechnology Limited, Surrey (GB)

( * ) Notice: Subject to any disclaimer, the term of this patent is extended or adjusted under 35 U.S.C. 154(b) by 0 days.

(21) Appl. No.: 09/851,419

(22) Filed: May 9, 2001

(65) Prior Publication Data

US 2002/0042134 A1 Apr. 11, 2002

Related U.S. Application Data

(60) Provisional application No. 60/207,275, filed on May 30, 2000.

(30) Foreign Application Priority Data

May 9, 2000 (GB) .............................. 0011186

(51) Int. Cl.$^7$ ............................ C12P 21/00; C12P 7/06; C12N 1/21
(52) U.S. Cl. .................. 435/69.1; 435/320.1; 435/132; 435/161; 435/183; 435/243; 435/252.1; 435/252.3; 435/252.31; 435/252.33
(58) Field of Search ............................ 435/320.1, 69.1, 435/4, 6, 91.1, 91.4, 91.41, 132, 161, 183, 243, 252.1, 252.3, 252.31, 252.33

(56) References Cited

U.S. PATENT DOCUMENTS 4,617,266 A * 10/1986 Fahnestock

FOREIGN PATENT DOCUMENTS

EP 370 023 5/1990

OTHER PUBLICATIONS

Macaluso et al., J. Bacteriol., 1991, vol. 173, No. 3, pp. 1353–1356.*
Walter et al., Annals New York Acad. Sciences, 1994, vol. 721, pp. 69–72.*
De Feyter, R., et al., Journal of Bacteriology (1991) vol. 173, No. 20, pp 6421–6427, "Use of Cloned DNA Methylase Genes to Increase the Frequency of Transfer of Foreign Genes into *Xanthomonas campestris* pv. Malvacearum".
Mermelstein, L.D., et al., Applied and Environmental Microbiology, Apr. 1993, vol. 59, No. 4, pp 1077–1081, "In Vivo Methylation in *Escherichia coli* by the *Bacillus subtilis* Phage Φ3T I Methyltransferase To Protect Plasmids from Restriction upon Transformation of *Clostridium acetobutylicum* ATCC 824".
Cue et al., Applied Environmental Microbiology, vol. 63, No. 4, pp 1406–1420, Apr. 1997; "Genetic Manipulation of *Bacillus methanolicus*, a Gram–Positive, Thermotolerant Methylotroph".

Narumi et al (1992) Biotechnology Techniques vol. 6, No. 1, pp 83–86; "A Newly Isolated *Bacillus stearothermophilus* K1041 and its Transformation by Electroporation".
Zeiss, S., (1991) PhD. thesis, Center for Biotechnology, Imperial College of Science, Technology and Medicine, London, pp. 1–196, "Genes and Enzymes of *Bacillus stearothermophilus* LLD".
Tang et al. (1994) Nucleic Acids Research, vol. 22, No. 14, p. 2857, "The optimization of preparations of competent cells for transformation of *E.coli*".
Konings, W.N. et al., (1983) Whittenbury and Wimpenny, Society for General Microbiology Symposium 34, pp. 153–186, Cambridge University Press, "Energy Transduction and Solute Transport Mechanisms in Relation to Environments Occupied by Microorganisms".
Padan, E. et al. (1981) Biochemica et Biophysica, Acta, 650, pp 151–166, "pH Homeostasis in Bacteria".
Sundaram, T.K. (1986) General, Molecular and Applied Microbiology Ed. Brock, T.D. John Wiley and Sons, Inc.), "Physiology and Growth of Thermophilic Bacteria".
Poindexter, J., The Public Health Research Institute of the City of New York, Inc., New York, pp 283–317, "Bacterial Responses to Nutrient Limitation".
Rowe, J., et al., Journal of Bacteriology, Oct. 1975, pp 279–284, vol. 124, No. 1, "Development of Defined and Minimal Media for the Growth of *Bacillus stearothermophilus*".
Lee, Y., et al., Journal of Applied Bacteriology, 1982, 53, pp 179–187, "Defined Minimal Media for the Growth of prototrophic and auxotrophic strains of *Bacillus stearothermophilus*".
Jurado, A., et al., Journal of General Microbiology (1987), vol. 133, pp 507–513, "Influence of Divalent Cations on the Growth and Morphology of *Bacillus stearothermophilus*".
Amartey, S., et al., Biotechnology Letters, 1991, vol. 13, No. 9, pp 621–626, "Development and Optimization of a Defined Medium for Aerobic Growth of *Bacillus stearothermophilus* LLD–15".
San Martin, R., et al., Journal of General Microbiology, 1992, vol. 138, pp 987–996, "Development of a synthetic medium for continuous anaerobic growth and ethanol production with a lactate dehydrogenase mutant of *Bacillus stearothermophilus*".

(List continued on next page.)

Primary Examiner—David Guzo
(74) Attorney, Agent, or Firm—Banner & Witcoff, Ltd.

(57) ABSTRACT

Sporulation-deficient variants of thermophilic, facultatively anaerobic, Gram-positive bacteria can be generated using a plasmid transformation system based on a novel method of in vivo methylation. Such bacteria exhibit improved ethanol production-related characteristics.

16 Claims, 3 Drawing Sheets

OTHER PUBLICATIONS

Baker, H., et al., Journal of General Microbiology, 1953, vol. 9, pp 485–493, "Growth Requirement of some Thermophilic and Mesophilic Bacilli".

Danilevich, V.N., et al., Molecular Biology, 1994, vol. 28, No. 1, Part 2, pp 105–110, "Construction of Recombinant Plasmids for Efficient Expression of the Pyruvate Decarboxylase Gene (pdk) from *Zymomonas mobilis* in *Bacillus subtilis*".

Payton, M., et al., FEMS Microbiology Letters 26, 1985, pp 333–336, "Mutants of *Bacillus stearothermophilus* lacking in NAD–linked L–lactate dehydrogenase".

Lerner, C.G., et al., Nucleic Acids Research, 1990, Oxford University Press, vol. 18, No. 15, p. 4631 "Low copy number plasmids for regulated low–level expression of cloned genes in *Escherichia coli* with blue/white insert screening capability".

\* cited by examiner

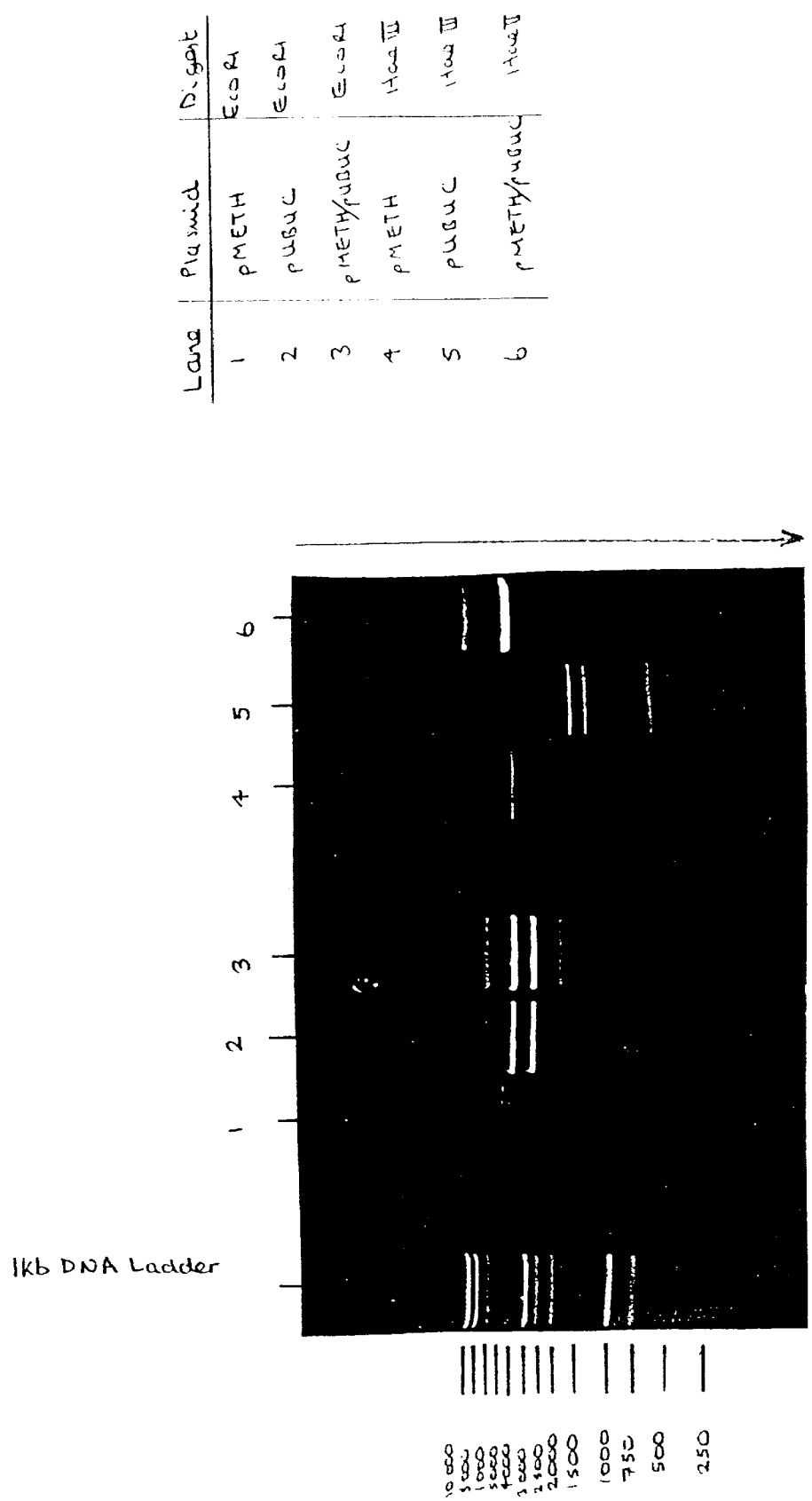
FIG. 3  EcoRI and HaeIII restriction digests of methylated and unmethylated plasmid DNA

MODIFICATION OF BACTERIA

This application is a continuing application of U.S. Provisional Patent Application Ser. No. 60/207,275, filed May 30, 2000, which is based on U.K. Application No. 0011186.4, filed May 9, 2000.

This invention relates to a novel method of in vivo methylation of nucleic acids. In particular, the invention relates to thermophilic Bacillus strains transformed using a plasmid transformation system based on the method of in vivo methylation. The invention can be used to increase ethanol production.

Many bacteria have the ability to ferment simple hexose sugars into a mixture of acidic and pH-neutral products via the process of glycolysis. The glycolytic pathway is universal and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. Under aerobic conditions (oxygen available), pyruvate is first oxidised to acetyl CoA and then enters the tricarboxylic acid cycle (TCA) which generates synthetic precursors, $CO_2$ and reduced cofactors. The cofactors are then oxidised by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidised in reactions involving the reduction of organic substrates to products such as lactate and ethanol. In addition, ATP is regenerated from the production of organic acids such as acetate in a process known as substrate level phosphorylation. Therefore, the fermentation products of glycolysis and pyruvate metabolism include a variety of organic acids, alcohols and $CO_2$.

The majority of facultatively anaerobic bacteria do not produce high yields of ethanol either under aerobic or anaerobic conditions. Most faculatative anaerobes metabolise pyruvate aerobically via pyruvate dehydrogenase (PDH) and the tricarboxylic acid cycle (TCA).

Under anaerobic conditions, the main energy pathway for the metabolism of pyruvate is via pyruvate-formate-lyase (PFL) pathway to give formate and acetyl-CoA. Acetyl-CoA is then converted to acetate, via phosphotransacetylase (PTA) and acetate kinase (AK) with the co-production of ATP, or reduced to ethanol via acetalaldehyde dehydrogenase (AcDH) and alcohol dehydrogenase (ADH). In order to maintain a balance of reducing equivalents, excess NADH produced from glycolysis is re-oxidised to $NAD^+$ by lactate dehydrogenase (LDH) during the reduction of pyravate to lactate. NADH can also be re-oxidised by AcDH and ADH during the reduction of acetyl-CoA to ethanol but this is a minor reaction in cells with a functional LDH. Theoretical yields of ethanol are therefore not achieved since most acetyl CoA is converted to acetate to regenerate ATP and excess NADH produced during glycolysis is oxidised by LDH.

Ethanologic organisms, such as *Zymomonas mobilis* and yeast, are capable of a second type of anaerobic fermentation, commonly referred to as alcoholic fermentation, in which pyruvate is metabolised to acetaldehyde and $CO_2$ by pyruvate decarboxylase (PDC). Acetaldehyde is then reduced to ethanol by ADH regenerating $NAD^+$. Alcoholic fermentation results in the metabolism of 1 molecule of glucose to two molecules of ethanol and two molecules of $CO_2$. DNA which encodes both of these enzymes in *Z. mobilis* has been isolated, cloned and expressed recombinantly in hosts capable of producing high yields of ethanol via the synthetic route described above.

A key improvement in the production of ethanol using biocatalysts can be achieved if operating temperatures are increased to levels at which the ethanol is conveniently removed in a vaporised form from the fermentation medium. However, at the temperatures envisioned, traditional mesophilic microorganisms, such as yeasts and *Z. mobilis,* are incapable of growth. This has led researchers to consider the use of thermophilic, ethanologenic bacteria such as Bacillus sp as a functional alternative to traditional mesophilic organisms. See EP-A-0370023.

The use of thermophilic bacteria for ethanol production offers many advantages over traditional processes based upon mesophilic ethanol producers. Such advantages include the ability to ferment a wide range of substrates, utilising both cellobiose and pentose sugars found within the dilute acid hydrolysate of lignocellulose, as well as, the reduction of ethanol inhibition by continuous removal of ethanol from the reaction medium using either a mild vacuum or gas sparging. In this way, the majority of the ethanol produced may be automatically removed in the vapour phase at temperatures above 50° C. allowing the production phase to be fed with high sugar concentrations without exceeding the ethanol tolerance of the organism, thereby making the reaction more efficient. The use of thermophilic organisms also provides significant economic savings over traditional process methods based upon lower ethanol separation costs.

The use of facultative anaerobes also provides advantages in allowing a mixed aerobic and anaerobic process. This facilitates the use of by-products of the anaerobic phase to generate further catalytic biomass in the aerobic phase which can then be returned to the anaerobic production phase.

It is possible that organisms which carry out glycolysis or a variant thereof can be engineered to divert as much as 50% of the carbon in a sugar molecule via glycolysis and a synthetic, metabolic pathway which comprises enzymes encoded by heterologous genes. The result is an engineered organism which produces ethanol as its primary fermentation product.

The inventors have produced sporulation deficient variants of a thermophilic, facultatively anaerobic, Gram-positive bacterium which exhibit improved ethanol production-related characteristics. This has been achieved through the development of a plasmid transformation system based on a novel method of in vivo methylation.

The production of recombinant Bacillus sp, engineered to express a heterologous gene, has previously been hampered by a Hae III type restriction system that limited plasmid transformation.

In vivo methylation has been used previously to overcome different restriction problems in other bacteria such as *Xanthomonas campestris*. For example, De Feyter and Gabriel (De Feyter, R, Gabriel, D. W.) Journal of Bacteriology 173 (1991) (20): 6421-7 have shown that where cosmid libraries of DNA from the bacterium *X. campestris* were restricted when introduced into strains of *Escherichia coli,* the use of cloned DNA methylase genes increased the frequency of transfer of foreign genes into *X. campestris* pv.

*malracearum*. In this instance, restriction was associated with the mcrBC+ gene in *E. coli*. Restriction was overcome using a plasmid (pUFRO52) encoding the XmaI and XmaIII DNA methylases isolated from *X. campestris* pv *malracearum*. Subsequent plasmid transfer from *E. coli* strains to *X. campestris* pv. *malvacearum* by conjugation was significantly enhanced.

Similarly, Mermelstein and Papoutsakis (Mermelstein, L. D, and Papoutsakis, E. T) Appl. Environ. Biology 59(4) (1993) have shown that in vivo methylation in *E. coli* by *B.subtilis* phage phi 3TI methyltransferase can be used to protect plasmids from restriction upon transformation of *Clostridium acetobutylicum*.

Transformation efficiency in Bacillus strains was initially limited by a HaeIII-type restriction system, previously identified in Bacillus strain LLD-R. Bacillus strain LLD-R possesses a powerful HaeIII type restriction-modification system similar to that found in *Haemophilus aegyptius* (Zaidi S. H. E. (1991) PhD thesis, Imperial College, London). The HaeIII restriction endonuclease methylates the inner cytosine residues in the recognition site S-GGCC-3 which occurs frequently in the GC rich genome of LLD-R. HaeIII restriction of heterologous plasmid DNA in strain LLD-R presented a major barrier to successful transformation as previous attempts to transform this strain with un-methylated DNA had failed. The inventors partially overcame the problem of heterologous plasmid DNA restriction via the in vitro methylation of plasmid DNA using a commercially available DNA HaeIII methylase. However, in vitro methylation was found to be highly unreliable, costly and time consuming.

*Bacillus methanolicus* has been transformed using plasmid DNA that has been methylated in vitro or in vivo by a host cell having an endogenous dam methylase (Cue et al, Appl. Environ. Microbiology, 63, 1406-1420, 1997).

The inventors have completely overcome the problem of heterologous plasmid DNA restriction using a novel method of in vivo methylation. Complete methylation of heterologous DNA was achieved using an in vivo methylation system incorporating the gene encoding HaeIII methyltransferase from *Haemophilus aegyptius*. The HaeIII methyltransferase gene was expressed from a compatible plasmid (pMETH) alongside a co-resident shuttle vector (pUBUC) in *E. coli*. In vivo methylated pUBUC was then used to transform Bacillus strains LLD-R, LN and TN. In vivo methylated pUBUC transformed Bacillus strains LLD-R, LN and TN at significantly higher frequencies than in vitro methylated pUBUC. No transformants were obtained with unmethylated plasmid DNA. Due to the fact that the in vivo methylation system only protects HaeIII restriction sites it is highly specific to the method embodied in the current invention.

Once the problem of heterologous plasmid DNA restriction had been overcome the inventors set out to optimise the plasmid transformation system. The inventors used a method of plasmid transformation based upon electroporation as this had previously been used for transformation of *B. stearothermophilus* strain K1041, Narumi et al (1992) Biotechnology Techniques 6 No. 1. This method of plasmid transformation was unsuccessful when used with Bacillus strains LLD-R, and TN until the electroporation conditions were optimised and the composition of the regeneration medium was changed. Surprisingly, by changing the electric field from 12.5 kV/cm to 5.0 kV/cm the inventors increased the plasmid transformation efficiency by 10 fold.

The inventors have isolated a transformable sporulation deficient mutant of Bacillus strain LLD-R. Isolation of this mutant removed a further barrier to transformation caused by sporulation, whereby cells readily sporulate after electroporation, inevitably reducing transformation frequency and transformant recovery. The inventors have also developed a shuttle vector which is able to replicate in both *E. coli* and Bacillus strains, and have developed a novel in vivo plasmid HaeIII methylation system to overcome restriction of heterologous plasmid DNA. The inventors have also developed a reliable and reproducible agar plate medium containing glycerol and pyruvate for aerobic growth of Bacillus strains LLD-R, LN, TN and derivatives thereof. This medium is referred to as TGP. Specifically, the production of organic acids, especially acetate, from sugars in growth media on agar plates has a significant effect upon culture growth and/or viable cell counts. The unpredictable nature of microorganism growth on agar plate media can be explained by the production of organic acids. These acids act to reduce the pH of the growth medium inhibiting cell growth and viability.

The inventors have overcome this problem by developing a growth medium comprising glycerol and/or pyruvate as non-fermentable carbon substrates. The addition of glycerol and/or pyruvate prevents anaerobic fermentation and production of organic acid by-products, thereby reducing the effects of organic acids, such as acetate, on the pH of the growth medium. In this way, viable cell counts obtained on agar plates using the TGP medium have been significantly increased when compared to cell counts obtained on mineral salt mediums and complex mediums containing fermentable sugars such as glucose, sucrose and xylose. The use of TGP medium increases subsequent transformation frequencies, on the basis of higher levels of cell viability, and provides a suitable medium for the short term maintenance of Bacillus strains of the present invention.

These four developments have been combined to produce a novel plasmid transformation system based on in vivo methylation for Bacillus strains LLDR, TN and LN.

Accordingly, a first aspect of the present invention relates to a method of producing a recombinant *Escherichia coli* comprising in vivo methylation in a host cell by a non-endogenous DNA methylase of a heterologous gene and introducing that in vivo methylated gene into a Bacillus. The heterologous gene is preferably involved in ethanol production. The Bacillus may be a thermophile. Preferably, the Bacillus is selected from *B. stearothermophilus; B. calvodex; B. caldotenax; B. thermoglucosidasius; B. coagulans; B. licheniformis; B. thermodenitrificans* and *B. caldolyticus*. The Bacillus may be sporulation deficient.

The heterologous gene may be methylated in any suitable host cell, preferably another bacterium, prior to the introduction of that gene into the Bacillus. For example, the host may be *E. coli*.

The host cell contains a non-endogenous DNA methylase enzyme to be used to methylate the heterologous gene. The DNA methylase may be a HaeIII methyltransferase. The use of modified enzymes and synthetic equivalents is within the scope of the invention.

The term "non-endogenous" means that the methylase is heterologous to the host cell i.e. the methylase is not normally produced by the host cell. Preferably the DNA methylase is heterologously expressed in the host cell. For example, the DNA methylase may be expressed from a plasmid in the host cell or from a heterologous methylase gene incorporated into the host cell's genome. A preferred plasmid is pMETH.

A shuttle vector which is able to replicate in both the host cell and the Bacillus may be used to transfer the methylated heterologous gene between the bacteria. A preferred shuttle vector is pUBUC.

The methylated heterologous gene may be incorporated into the chromosome of the recombinant Bacillus sp.

According to another aspect of the invention, there is provided a method for transforming a Gram-positive bacteria comprising using electroporation at a voltage of about 4.0 to 7.5 kV/cm.

According to another aspect of the invention, there is provided a Bacillus sp which has been transformed with a methylated heterologous gene. The Bacillus may be a thermophile.

Preferred Bacillus include B. stearothermophilus; B. calvodex; B. caldotenax; B. thermoglucosidasius; B. coagulans; B. licheniformis; B. thermodenitrificans and B. caldolyticus. Preferably, the Bacillus is sporulation deficient.

According to another aspect of the invention there is provided a method for the production of a novel agar plate medium for the aerobic growth of Bacillus strains of the invention comprising, addition of a non-fermentable carbon source. The non-fermentable carbon source is preferably glycerol and/or pyruvate.

Aerobic growth of Bacillus strains on the agar medium results in a reduction of the amount of organic acid by-products produced, thereby preventing a reduction in the pH levels of the growth medium, resulting in more consistent and increased cell counts, thereby increasing subsequent transformation frequencies.

BRIEF DESCRIPTION OF THE DRAWINGS

The production of recombinant bacteria in accordance with the invention will now be described, by way of example only, with reference to the accompanying drawings, FIGS. 1 to 3 in which:

FIG. 3 illustrates agarose gel electrophoresis of EcoRI and HaeIII restriction digests of methylated and unmethylated plasmid DNA from three plasmid preparations (PMETH, pMETH/pUBUC and pUBUC). Lanes 1-3 are EcoRI digests of pMETH, pUBUC and pMETH/pUBUC respectively. Lanes 4-6 are HaeIII digests of pMETH, pUBUC and pMETH/pUBUC respectively.

Figure 1:
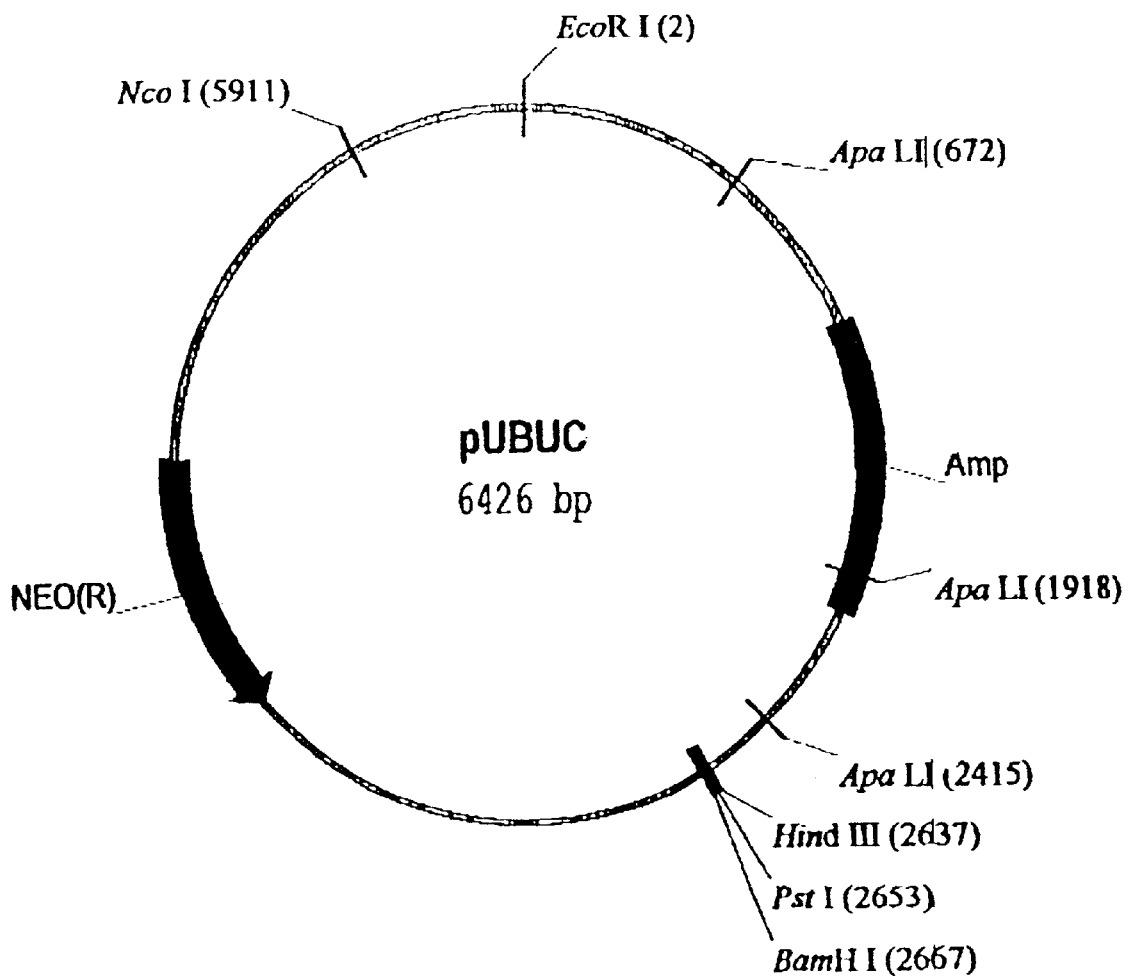
FIG. 1 is a schematic representation of shuttle vector pUBUC.

EXAMPLE 1
Strains, Plasmids and Growth Conditions
The strains and plasmids used are set out in Table 1:

TABLE 1

| Strain | Relevant Characteristics | Source/Reference |
|---|---|---|
| Haemophilus aeygptius | | NCIMB |
| Escherichia coli TOP10 | | Invitrogen |
| Escherichia coli HM2 | Methylation strain harbouring pMETH | Agrol Limited |
| Bacillus strain LN | spo⁻mutant of LLD-R | Agrol Limited |
| Bacillus strain LLD-R | Parent Strain | Amartey et al., 1991, Biotechnol. Lett., 13, 621–626 |
| Bacillus strain TN | ldh⁻mutant of LLD-R | Agrol Limited |
| Bacillus strain K1041 | | Narumi et al 1982 |
| Bacillus strain LLD-15 | ldh-mutant | Payton M.A. & Hartley B.S. (1985) FEMS Microbiology Letters, 26, 335–336 |

TABLE 1-continued

| Strain | Relevant Characteristics | Source/Reference |
|---|---|---|
| Bacillus strain LLD-16 | ldh-mutant | Javed, M. (1993) Centre for Biotechnology, Department of Biochemistry, Imperial College, London |
| Plasmid | | |
| pCL1920 | Sp$^R$ | (Lerner & Inouye, 1990) |
| pUB110 | Km$^R$ | Sigma |
| pUBUC | Km$^R$ | Agrol Limited |
| pUC18 | Ap$^R$ | Pharmacia |
| pMETH | Sp$^R$, met$^+$ | Agrol Limited |

E. coli TOP10 was grown aerobically at 37° C. in Luria-Bertani (LB) medium supplemented, as required, with ampicillin (50 µg/ml), kanamycin (50 µg/ml) and spectinomycin (50 µg/ml). Bacillus strains were grown aerobically at 52° C. in tryptone-glycerol-pyruvate (TGP) growth medium. Colonies were obtained on agar solidified TGP (20 g agar/l). TGP medium was supplemented, as required, with kanamycin (12 µg/ml).

EXAMPLE 2
Selection of Non-sporulating Mutants

Bacillus strain LLD-R was grown anaerobically under continuous conditions in a 2l vessel (LH 500 series) for approximately 200 hrs for selection of non-sporulating mutants. Samples were removed every 24 hrs and plated onto TGP agar plates. The culture was controlled at pH 7.0 (with 10% w/v sodium hydroxide), the growth temperature was maintained at 70° C. and the medium dilution rate was set at 0.1 h$^{-1}$. The culture was sparged with nitrogen (75 ml/min) and stirred at 400 rpm.

The inoculum was prepared from a single plate-derived colony in 50 ml of TGP medium and approximately 150 ml of exponentially grown culture (OD$_{600}$-2.0) were used to inoculate 1500 ml of BST growth medium.

The BST growth medium contained (per liter of deionised water) 0.32 g citric acid, 2.5 g disodium hydrogen orthophosphate (anhydrous), 0.27 g magnesium sulphate (heptahydrate), 1.3 g potassium sulphate, 2.0 g potassium nitrate (or 2.0 g ammonium chloride), 0.25 ml manganese chloride (tetrahydrate) (1.2% (w/v) stock solution), 0.25 ml calcium chloride (dihydrate) (1% (w/v) stock solution), 0.25 ml trace elements (TE) stock solution (see below), amino acids (150 mg of methionine, 150 mg of isoleucine, 150 mg of serine and 450 mg of glutamic acid), vitamins (1 mg of thiamine HCl, 0.45 mg riboflavin, 1.5 mg nicotinic acid, 0.45 mg pyridoxine HCl and 1 mg of biotin) and 10 g of sucrose. The trace elements, amino acids, vitamins and sucrose solutions were sterilised separately.

The TE stock solution contained (per liter of deionised water) 0.32 g zinc sulphate (monohydrate), 4.3 g ferric chloride (hexahydrate), 0.08 g boric acid, 0.4 g cobalt chloride (hexahydrate), 1.6 g copper sulphate (pentahydrate), 0.08 g nickel chloride (hexahydrate), 2 g EDTA. The TE stock solution was stored at 4° C.

The cultures were initially grown in 50 ml TGP medium at 70° C. for 3 hours until they reached an OD$_{600}$ of about 0.5.

Sporulation was induced by either temperature shock or nutrient limitation.

Temperature shock was induced by placing 10 ml aliquots of the culture in either ice, leaving at room temperature, 37° C., and 55° C. for 2 hours. The cultures were then re-incubated at 70° C. for a further 24 hours. A control culture was grown at 70° C. for 2 hours.

A 0.5 ml inoculum was used to inoculate 50 ml of BST medium containing 0.1% sucrose, and supplemented with 0.5% of either glutamic acid or histidine incubated at 70° C. for 48 hours. Samples were analysed for spore formation.

Spores were visualised after staining by microscopy (Zeiss Phase Contrast Microscope; ×100 oil objective). Staining was achieved using the malachite green spore stain. Approximately 10 μl of culture was heat fixed onto a microscope slide. The slide was flooded with malachite green (BDH) and steamed over a boiling water bath for 10 minutes. The slide was rinsed under tap water for 30 seconds and then counter stained for 1 minute with Gram's safranine solution (BDH). The slide was rinsed under tap water for 1 minute and dried at room temperature. Spores were stained green and vegetative cells stained red.

Bacillus strain LLD-R was grown anaerobically in continuous culture to select for non-sporulating mutants. The fermentation was started as a batch culture for 3 hours and then fed continuously with BST medium at a dilution rate of 0.1 h$^{-1}$ for approximately 10 volume changes. Samples were analysed at regular intervals for signs of sporulation. At the start of the feed (time 0), 12% of the cells had sporulated. This concentration decreased to 1% after 100 hours. The dilution rate was increased to 0.2 h$^{-1}$ and after another 100 hours (total time 200 hours) no spores were detected. A number of colonies were isolated from this sporulation deficient culture after overnight incubation at 70° C. on TGP plates.

The cultures were subjected to a variety of conditions that normally induce sporulation in LLD-R, stained and observed by microscopy. Sporulation was checked after temperature shock, and nutrient limitation. Strain LLD-R, the positive control sporulated under all test conditions whereas the mutant strain displayed no signs of sporulation. One culture remained sporulation minus under all growth conditions tested and was named as LN. This strain was used for subsequent transformations.

Sporulation frequency for strain LLD-R was related to incubation. The spore percentage after incubation at 4° C., 20° C., 37° C., 55° C. and at 70° C. were 94%, 55%, 54%, 22% and 1% respectively. However, such temperature shocks failed to trigger sporulation in the mutant strain cultures.

Sporulation was also induced in strain LLD-R during nutrient and carbon-limitation. The spore percentage after growth in glutamic acid and histidine was 37% and 17%, respectively. No growth was observed with histidine.

The glutamic acid grown culture was re-grown under the same growth conditions in fresh medium (without sucrose) and the spore percentage increased to 77%.

Previous results have shown that when potassium nitrate is used as the sole nitrogen source (instead of ammonium chloride) then sporulation is readily induced.

EXAMPLE 3
DNA Isolation, Manipulation and PCR Amplification

The manipulation, transformation and isolation of plasmid DNA from *E. coli* was performed using standard procedures (Maniatis). Plasmid isolation was undertaken from *E. coli* and Bacillus strains using a plasmid purification kit (Qiagen®). PCR purification and DNA gel purification were performed using kits (Qiagen®). The restriction and modifying enzymes were used in accordance with the manufacturer's recommendations (Promega®). HaeIII methylase was used in accordance with the manufacturers recommendations (New England Biolabs®). DNA ligation was performed using the Rapid Ligation Kit in accordance with the manufacturers recommendations (Roche Diagnostics).

The methylase gene was amplified from H aegyptius chromosomal DNA by PCR. The concentration of reactants and the PCR procedure used were those recommended in the Expand™ High Fidelity PCR System (Boebringer Mannheim). PCR amplification from lyopholized cells was achieved after 30 cycles in a Genius thermocycler (Techne®, Ltd., Cambridge). The upstream primer Hae111-F2, was 5'-TCTAGAGGAGGATTTTATGAATTTA-3' (SEQ ID NO:1) and the downstream primer, Hae111-R2 was 5'-GGATCCTTTCGATATTATATTCTG-3' (SEQ ID NO:2). An XbaI site and an *E. coli* ribosomal binding site were introduced into the upstream primer. A BamH1 restriction site was introduced into the downstream primer (underlined).

EXAMPLE 4
Construction of pUBUC

A shuttle vector for the transfer of DNA between *E. coli* and Bacillus strains was developed by fusing pUC18 and pUB110. Plasmid pUB110 is a widely used vector that was isolated from *Staphyloccocus aureus* and confers resistance to kanamycin and can replicate in *B. stearothermophilus* at temperatures up to 54° C. (Narumi et al., 1992 Biotechnology Techniques 6, No. 1). Plasmids pUB110 and pUC18 were linearised with EcoR1 and BamIl1, and then ligated together to form pUBUC (6.4 kb) (FIG. 1). Plasmid pUBUC has a temperature sensitive replicon, and cannot replicate above 54° C. making it an ideal host for gene integration, via homologous recombination at elevated temperatures. This plasmid was used to transform *E. coli* and Bacillus strains.

EXAMPLE 5
Construction of pMETH

A 1.1 kb fragment containing the met gene was amplified from *H. aeygptius* chromosomal DNA by PCR. The sequence was verified by DNA sequencing. The met gene was trimmed with BamH1 and XbaI, and then subcloned into the expression plasmid pCL1920, previously linearised with BamH1 and Xba1. The resultant plasmid pMETH (FIG. 2) was transformed into *E. coli* TOP10. *E. coli* TOP10 cells harboring pMETH were propagated and the culture was harvested for subsequent transformation and in vivo methylation using a method described by Tang et al (1994) Nuc. Acid Res. 22 (14). Competent cells were stored in convenient aliquots at −70° C. prior to transformation.

EXAMPLE 6
DNA Methylation and Strain Transformation

The methylase gene was first amplified and cloned with the native promoter sequence. However, the gene from this construct was poorly expressed and only resulted in partial DNA methylation. The met gene was then placed under the control of a lac promoter in pMETH. Sufficient expression and plasmid methylation was achieved without IPTG induction.

In vitro methylation of pUBUC was achieved using HaeIII methylase in accordance with the manufacturer's (New England Biolabs) instructions. In vivo methylation of pUBUC was achieved after transformation, propagation in, and purification from *E. coli* TOP10 harboring pMETH. Plasmids pUBUC and pMETH were maintained with ampicillin and spectinomycin, respectively. Plasmid pUBUC, isolated from *E. coli* TOP10, was used as an unmethylated control.

The integrity and degree of methylation of plasmid pUBUC was verified by EcoRI/BamHI and HaeIII plasmid digests. Digests from three plasmid preparations (pMETH, pMETH and pUBUC, and pUBUC) were analysed by agarose gel electrophoresis (FIG. 3).

According to the plasmid map, EcoRI digests of pMETH should generate two fragments of 1.5 kb and 4.7 kb, pUBUC should yield two fragments of 2.7 kb and 3.8 kb, and the pUBUC/pMETH mixture should yield four fragments of 1.5 kb, 2.7 kb, 3.8 kb and 4.7 kb. An EcoRI digest of pMETH (FIG. 3, lane 1) produced only one visible fragment of the correct size. The smaller band was difficult to see due to the low DNA yield. An EcoRI digest of pUBUC (FIG. 3, lane 2) produced two visible fragments of the expected size. An EcoRI digest of the plasmid mix of pUBUC and pMETH (FIG. 3, lane 3) produced five visible fragments, four of which were the correct size. The larger fragment is probably an incomplete digest. These EcoRI digests verify the integrity of the plasmid DNA and indicate that the DNA was pure enough for enzyme digestion.

All three plasmid preparations were then digested with HaeIII (FIG. 3, lanes 4-6). Plasmids pMETH (FIG. 3, lane 4) and the pUBUC/pMETH mixture (FIG. 3, lane 6) were resistant to HaeIII digestion indicating that pUBUC and the co-resident pMETH, isolated from *E. coli*, were fully methylated and protected from HaeIII digestion. In contrast, the unmethylated control pUBUC (FIG. 3, lane 5) was digested into several small fragments.

Co-expression of the met gene (from pMETH) produced sufficient methylase to methylate and protect all HaeIII restriction sites present in pUBUC. In vivo methylation proved to be a reliable and inexpensive technique for DNA methylation. In addition, in vivo methylated plasmid DNA was readily transformed in Bacillus strains LLD-R, TN and LN.

The transformability of Bacillus strains LLD-R, TN, K1041 and LN were compared using methylated pUBUC. The transformation efficiencies obtained with LLD-R, TN, K1041 and LN were 30, 20, 1 and 205 transformants per $\mu$g of DNA, respectively. The transformability of strain LN with pUBUC was approximately seven times higher than its parent LLD-R and ten times higher than the ethanol producing mutant TN. Strain LN is the most transformable strain, but strains LLD-R and the ethanol producing mutant TN are also amenable to transformation albeit at lower frequencies. The transformation frequencies with LN are reproducible and high enough to allow for further optimization of the electro-transformation procedure which, in turn should increase the transformability of other strains. Ten transformants were isolated from strains LLD-R, LN and TN, and grown overnight in TGP with kanamycin. Plasmid DNA, isolated from the cultures, was checked by restriction analysis and found to be identical to pUBUC isolated from *E. coli*.

The degree of methylation of pUBUC greatly affected the transformation efficiency (See Table 2).

TABLE 2

| Source of pUBUC | Transformants/ug DNA |
|---|---|
| Control (no plasmid) | 0 |
| Unmethylated (from *E. coli*) | 0 |
| Methylated (in vitro) | 5 |
| Methylated (from LN) | 201 |
| Fully Methylated (from *E. coli* (pMETH)) | 189 |

It was possible to transform Bacillus strain LN with pUBUC isolated from LLD-R, but not with un-methylated pUBUC isolated from *E. coli*. Despite the low concentration of DNA isolated from LLD-R (30 $\mu$g/ml), the transformation efficiency was relatively high. This suggests that Bacillus strain LLD-R contains a restriction/modification system preventing transformation of unmodified DNA.

Plasmid DNA was partially methylated in-vitro, after three incubations with HaeIII methylase. Transformants were obtained but the transformation frequency was relatively low. However, when the plasmid DNA was methylated in vivo, the transformation frequency increased 30-fold to a level comparable with DNA isolated from LLD-R. Moreover, methylated pUBUC is a plasmid mixture containing the low copy number plasmid pMETH and the transformation efficiencies observed do not take into account the concentration of pMETH. The frequencies obtained from the in vivo methylation procedure are therefore underestimated. No transformants were obtained with methylated pMETH and water (no DNA) controls.

EXAMPLE 7

Electro-transformation of Bacillus Strains

Cells were grown at 60° C. in 75 ml of TGP medium until the absorbance at 600 nm ($A_{600}$) reached 0.3-0.9 (preferably 0.6). The culture was chilled on ice for 15-30 min. The cells were harvested by centrifugation and washed once in 10 ml and twice in 5 ml of cold TH buffer (272 mM trehalose and 8 mM HEPES; pH 7.5 with KOH). The cell pellet was resuspended in 400 $\mu$l of TH buffer and stored at 4° C. prior to electroporation. Methylated plasmid DNA was used to transform Bacillus strains by electroporation based on a method previously described by Narumi et al (1992) Biotechnology Techniques 6(1). The competent cells were dispensed into 90 $\mu$l aliquots and mixed with 2-8 $\mu$l (preferably 4 $\mu$l) DNA (250 ng/$\mu$l). The mixture was transferred to cold electroporation cuvettes with 0.2 or 0.4 cm electrode gap (preferably 0.2 cm). The suspensions were then subjected to a 0.8-2.5 kV (preferably 1.1 kV) discharge from a 25 $\mu$F or 0.5 $\mu$F (preferably 25 $\mu$F) capacitor and the pulse control was set at 156-2310 ohms (preferably 481 ohms) with the time constant ($\tau$)=4-57.7 msec (preferably 12 msec) using a EquiBio EasyJect electroporator. Immediately after electroporation, 400 $\mu$l pre-warmed TGP was added to the curvette and the contents of the cuvette was then transferred to 4 ml pre-warmed TGP in 15 ml Falcon tubes. The cells were incubated at 52° C. with shaking at 210 rpm for 0-120 min (preferably 90 min) and plated onto TGP agar supplemented with 0-20 $\mu$g/ml kanamycin (preferably 12 $\mu$g/ml). The plates were incubated for 24-48 hours at 52° C. The transformation efficiency was calculated as the average number of colonies obtained per $\mu$g of methylated plasmid DNA.

EXAMPLE 8

Development of TGP: A High Efficiency Plating Medium for the Growth of Thermophilic Bacillus Strains The nutritional requirements for Bacillus strains differ under aerobic and anaerobic conditions, and in the presence of different carbon substrates. Aerobically grown cultures on sucrose require methionine, biotin, nicotinic acid and thiamine besides mineral salts and a carbon source (Amartey S. A. et al (1991) Biotechnol Lett, 13 (9), 621-626) while anaerobic cultures additionally require glutamate, isoleucine, serine, pyridoxine and riboflavin (San Martin R et al (1992) J Gen Micrbiol, 138, 987-996). Although these nutritional supplements defined for the growth of anaerobic cultures on sucrose as a carbon source can support the growth of anaerobic cultures on other hexose monomer and dimer sugars, the anaerobic growth on xylose requires a further addition of aspartate (Javed, M (1993) Centre for Biotechnology, Department of Biochemistry, Imperial College, London). Although a number of growth media have been developed for the cultivation of thermophilic microorganisms, almost all of them concentrate on defining the requirements for amino acids, vitamins, and mineral salts (Baker. H, et al (1953) J Gen Microbiol, 9, 485-493; Jurado, A. S. et al (1987) J Gen Microbiol, 133, 507-513; Lee, Y. H. et al (1982) J Appl Bacteriol, 53, 179-187; Rowe, J. J. et al (1975) J Bacteriol, 124, 279-284) there are very few reports on the development of agar plate medium for thermophiles using dual carbon substrates.

Variations in the number of viable cell counts was investigated under aerobic growth conditions on agar plate mediums containing single or dual carbon substrates. The addition of dual carbon substrates to the growth medium generally showed a diauxic growth, but they can be useful especially when the presence of the second substrate helps to detoxify the effect of the first substrate or its product (Poindexter, J. S. 1987 SGM 41, pp 283-317. Academic Press, New York Inc.).

Microgranisms and Growth Conditions

The Bacillus strains used in this study are described in Table 1.

Cultures were maintained on nutrient agar plates and routinely subcultured every 3-4 weeks. The growth temperature for all the experiments was 70° C. unless otherwise specified.

Mineral Salt (MS) Medium contained (per liter of deionised water) 0.32 g of citric acid, 2.0 g of disodium hydrogen orthophosphate (anhydrous) 0.4 g of magnesium sulphate (heptahydrate), 0.3 g of potassium sulphate, 2.0 g of ammonium chloride, 0.003 g of manganese chloride (tetrahydrate), 0.007 g of ferric chloride and 1.0 ml of trace elements stock solution (TE).

Trace elements (TE) stock solution contained (per liter of deionised water) 0.4 g of zinc sulphate (heptahydrate), 0.01 g of boric acid, 0.05 g of cobalt chloride (hexahydrate), 0.2 g of copper sulphate (pentahydrate), 0.01 g of nickel chloride (hexahydrate), 0.5 g of ferrous sulphate (heptahydrate), 0.25 g of EDTA.

Methionine stock solution contained (per liter of deionised water) 20 g of methionine.

Vitamin stock solution contained (per liter of deionised water) 15 g of nicotinic acid, 10 g of thiamine hydrochloride and 10 g of biotin.

Defined Mineral Salts Medium contained MS medium with 1 ml/L of each of the vitamin and methionine stock solutions.

TGP Medium contained (per liter of deionised water) 17 g tryptone, 3 g soya peptone, 2.5 g of potassium di hydrogen phosphate, 5 g of sodium chloride, 4 g of sodium pyruvate and 4 ml of glycerol; pH 7.0.

Nutrient Agar (Difco Company Ltd)

Yeast extract-Tryptone (YT) Medium contained (per liter of deionised water) 25 g of yeast extract, 12.5 g of tryptone and 200 mL of separately sterilised phosphate buffer (3.4% potassium di hydrogen phosphate, adjusted to pH 7.0 with NaOH).

Physiological Saline Solution: 9.0 g of sodium chloride in 1000 mL of distilled water adjusted to pH 7.0 with dilute sodium hydroxide solution and autoclaved.

Chemostat Culture: The chemostat cultures were set up as described by San Martin, R et al (1992) J Gen Microbiol, 138, 987-996.

Analytical Methods: Organic acids were determined using the method described by Shama G & Drumond I. W. (1982) Chromatographia, 15, 180). Optical density was measured by Novaspec 4049 Spectrophotometer (LKB Biochrom). Culture pH was routinely measured using a pH meter (Data Scientific Co. Ltd. UK).

Carbon Source: Defined and Semi-Defined media contained carbon source(s) which are described in the text. Their concentrations were 10 g/L when used as a single carbon substrate and 0.5 g/L each when used as dual carbon substrates. All plate media contained 20 g/L bacto agar as a solidfying agent.

Growth of Bacillus Strains at Different pH Values

FIG. 4 shows that the minimum growth pH for these bacterial strains is 6.1.

FIG. 4 also shows that maximum biomass concentrations were obtained when strains were grown at a pH between 7.0 and 7.5 and the working pH range for their growth is between 6.1 and 8.5.

TABLE 3

Shows the steady state concentrations of organic acids produced by LLD-16 in chemostat culture under aerobic and anaerobic conditions in MS medium containing 1 g/L yeast extract and 10 g/L xylose at a dilution rate of 0.19 $h^{-1}$, pH 7.0, 70° C. The anaerobic bioreactor was sparged with nitrogen gas at the rate 0.1 VVM and stirred at an agitation rate of 400 rpm. The aerobic bioreactor was sparged with air at the rate of 0.5 VVM and stirred at an agitation rate of 650 rpm.

| Growth condition | Formate (g/L) | Acetate (g/L) |
| --- | --- | --- |
| Anaerobic | 1.27 | 0.79 |
| Aerobic | 0.45 | 2.52 |

The ratio of formate to acetate was approximately 1.5:1 under anaerobic conditions and 1:5.5 under aerobic conditions.

Change in pH of the Medium During Growth in Shake Flasks

Strain LLD-16 was grown under aerobic conditions in Defined medium in shake flask cultures containing different carbon substrates. The results are shown in Table 4.

TABLE 4

Optical density at 600 nm ($OD_{600}$) and culture pH after 20 hours of aerobic growth of strain LLD-16 at 70° C. in Defined medium containing different carbon substrates.

| Carbon source | $OD_{600}$ | Final pH |
| --- | --- | --- |
| Glucose | 0.56 | 5.3 |
| Sucrose | 0.64 | 5.3 |
| Xylose | 0.55 | 5.2 |
| Glycerol | 0.48 | 6.4 |
| Pyruvate | 0.47 | 8.6 |

All carbon substrates were used at a concentration of 10 g/L.

Initial medium pH was set to 7.0±0.1.

The cultures were grown in 250 mL shake flasks containing 50 mL media and incubated in a shaking incubator at 250 rpm.

The pH of the culture fell from pH 7.0 to between 5.2 and 5.3 when the carbon substrate was a fermentable sugar such as glucose, sucrose, xylose. In the presence of glycerol as the carbon source, the pH descreased from 7.0 to 6.4 whereas when pyruvate was used as the carbon substrate, the pH of the medium culture increased from 7.0 to 8.6. A decrease in the culture pH is due to the production of organic acid(s) during growth on sugars whereas an increase in the pH of the medium during growth on pyruvate is attributed to the accumulation of excess of cations (sodium) in the medium as a result of utilisation of the anions (pyruvate) (Mandelstram J et al (1982) Biochemistry of Bacterial Growth. 3rd Ed, Blackwell Scientific Publications, Oxford).

Microoranisms can maintain their cytoplasmic pH within narrow limits over a wide range of external pH values (Konings, W. N and Beldkamp, H (1983) Whittenbury and Wimpenny, Society for General Microbiology Symposium 34, pp 153-186. Cambridge University Press). However, when high concentrations of acetate are produced during growth, and the extracellular pH drops, acetate will be present in the un-dissociated form and will diffuse back freely across the bacterial membrane into the cytoplasm (Kell, D. B et al (1981) Biochemical Research communications, 99, 81-88; Padan, E. et al (1981) Biochemica et Biophysica, Acta, 650, 151-166). This causes a lowering of the pH of the cytoplasm and inhibits bacterial cell growth.

Since the culture pH fell during growth on sugars and increased during growth on acid salt (pyruvate), it was envisaged that addition of the latter in the medium with one of the sugars as a carbon substrate would maintain the culture pH near neutral values during growth. However, the results (Table 5) show that the pH of the culture dropped quite significantly (from pH 7.0 to 5.5) in these media showing that the drop in the pH of the medium due to utilisation of the sugar was too acidic to be neutralised by utilisation of the pyruvate salt. Again, when glycerol was used as one of the carbon substrates, the pH of the medium remained close to its initial value (from pH 7.0 to 6.7). Though addition of pyruvate in these growth media did not affect the pH of the culture, its presence in such media on agar plates gave 2-3 fold higher numbers of viable cell counts than the media which only contained sugar as a carbon substrate (Table 6).

TABLE 5

$OD_{600}$ and culture pH after 20 hours of aerobic growth of LLD-16 in Defined medium containing different dual carbon substrates.

| Carbon source | $OD_{600}$ | Final pH |
| --- | --- | --- |
| Glucose + Pyruvate | 0.68 | 5.3 |
| Glycerol + Pyruvate | 0.50 | 6.7 |
| Xylose + Pyruvate | 0.70 | 5.5 |

All carbon substrates used were 5 g/L. Initial pH was set to 7.0±0.1. The cultures were grown at 70° C. in 250 mL. Shake flasks containing 50 mL medium and incubated in a shaking incubator at 250 rpm.

TABLE 6

Viable cell counts of LLD-16 after overnight aerobic growth at 70° C. on different agar plate media.

| Carbon substrate(s) used* | No. of colonies/mL culture ($OD_{600}$ = 1.0) |
| --- | --- |
| Sucrose | $1.5 \times 10^7$ |
| Glucose | $1.4 \times 10^7$ |
| Pyruvate | $2.7 \times 10^7$ |
| Glycerol | $4.0 \times 10^7$ |
| Glucose + pyruvate | $4.0 \times 10^7$ |
| Nutrient agar | $1.6 \times 10^7$ |

Apart from Nutrient agar, other media contained nutrients of defined medium + carbon substrate(s).
*Carbon source used 10 g/L if used as a single carbon substrate and 5 g/L each when used as a mixed carbon substrate.

Growth on Agar Plate Medium

Cells were grown in YT medium ot $OD_{600}$ of 1.0. The cells were harvested and washed once in MS medium (pH 7.0) and serial dilutions were made in the same medium. Each plate was spread with 100 μl of the suspension and incubated at 65° C. overnight. Viable cell counts obtained on different media are shown in Table 6.

On agar plate with Semi-Defined (SD) medium, addition of glucose as a carbon source gave the least number of viable cell counts ($1.2 \times 10^8$) while addition of dual carbon substrates, glycerol+pyruvate gave maxium number of viable counts ($5.6 \times 10^8$). Addition of glycerol or pyruvate in the medium alone gave intermediate values of viable cell counts. The YT medium plates gave even less numbers of viable cell counts than those obtained with SD medium containing glucose ($3.0 \times 10^7$ vs $1.2 \times 10^8$). However, addition of glycerol and pyruvate in the YT medium improved its plating effciencies by 10-fold. These results also show that higher concentrations of yeast extract and tryptone together, alone cannot give reliable cell counts until another carbon source is added.

An inoculum was also prepared by suspending a loopful of the LLD-16 culture from a Petri plate in a sufficient amount of normal saline solution (pH 7.0) to give an $OD_{600}$ of 1.0. The suspension was then serially diluted and plated on different agar media and incubated at 70° C. overnight. The viable cell counts on these media are shown in Table 7. The plate media containing fermentable carbon substrate, such as glucose or sucrose gave comparatively low viable cell counts ($1.5 \times 10^7$) while the media containing non-fermentable carbon substrate, glycerol or pyruvate, gave relatively higher viable cell counts. Among the media with single carbon substrate, addition of glycerol gave highest viable cell counts ($4.0 \times 10^7$). Addition of either pyruvate or acetate in the medium with sugar as the carbon substrate improved the plating efficiencies of these media by a factor of 2-3 fold, and the highest viable cell counts ($4.1 \times 10^7$) were obtained on the plates containing glycerol and pyruvate (0.5% each w.v).

TABLE 7

Viable cell counts of LLD-16 after overnight aerobic growth at 70° C. on different agar plate media.

| Media | No. of colonies/mL culture ($OD_{600}$ = 1/0) | Colony diameter (mm) |
| --- | --- | --- |
| Glucose | $1.2 \times 10^8$ | 2.5 |
| Pyruvate | $4.5 \times 10^8$ | 1.5 |
| Glycerol | $3.47 \times 10^8$ | 1.5 |
| Glycerol + Pyruvate | $5.6 \times 10^8$ | 3.5 |
| YT Medium | $3.0 \times 10^7$ | 5.0 |
| YT + Glycerol + pyruvate | $3.0 \times 10^8$ | 6.0 |

Apart from YT medium, other media contained nutrients of SD medium+carbon substrate(s). Carbon substrate concentrations were 10 g/L if used as a single carbon substrate and 5 g/L each when used as a dual carbon substrate.

By comparing the results shown in Table 6 with those of Table 7 (SD medium vs. Defined medium), it is clear that the viable cell counts on Defined medium plates were almost 10 times lower than those obtained on Semi-Defined medium. Hence, for reliable cell counts, addition of small amounts of yeast extract and tryptone in the agar plate medium seemed necessary. However, addition of larger amounts of these nutritional supplements might show an inhibitory effect on growth, as a lesser number of colonies grew on nutrient agar or YT agar plates (Tables 6 and 7). The reproducibility of the viable cell counts on the plate medium with fermentable carbon source or on YT plate medium was very poor. In many of our experiments, either a very small number of colonies or no colony grew on these plates. Moreover, plates grown with less diluted cultures gave lower viable cell counts compared to those which were spread with more diluted cultures. However, occasionally reliable cell counts were observed on these plates. Therefore, the viable cell counts presented in Tables 6 and 7 were taken from those plates which showed reliable cell counts and are not an average of different replicates.

If equivalent amounts of the cell suspension were plated on media containing sugars or media containing glycerol and/or pyruvate as the carbon source(s), the latter always gave reliable viable cell counts within experimental errors. The viable cell counts also matched well with the culture dilution factor.

Although the medium containing glycerol and acetate as carbon sources gave reliable viable cell counts (Table 7) and the pH of the medium in liquid culture did not drop significantly after 20 hours growth (Table 5), the colony morphology appeared to be on these plate media. Circular colonies were observed on all plate media except in the case of acetate where irregular shaped colonies with a rough surface were observed. For this reason, the medium with glycerol and pyruvate as a carbon source was preferred to the medium with glycerol and acetate.

Table 8 shows a comparison of viable cell counts of strain LLD-R and its different mutants on Semi-Defined plate media with glucose and glycerol+pyruvate as carbon sources. This shows that the plating efficiency of the medium with the glycerol plus pyruvate as carbon substrates was at least 3-fold higher than those with glucose as a carbon source for all the strains tested.

TABLE 8

A comparison of the plating efficiencies of Semi-Defined medium with glucose and with glycerol + pyruvate for LLD-R and its various mutants.

| Strain | Plating efficiency in SD medium with* | |
| --- | --- | --- |
|  | Glucose | Glycerol + Pyruvate |
| LLD-R | $1.2 \times 10^8$ | $5.3 \times 10^8$ |
| LLD-15 | $1.3 \times 10^8$ | $5.1 \times 10^8$ |
| LLD-16 | $1.1 \times 10^8$ | $4.9 \times 10^8$ |
| T13-N | $1.4 \times 10^8$ | $4.0 \times 10^8$ |

*After overnight growth at 70° C.

The production of organic acids, especially acetate, from sugars in the growth media or on the agar plates significantly affected the culture growth or viable cell counts. Cell growth either in liquid culture or on agar plates was unpredictable when the medium contained a fermentable sugar. Agar plate medium spread with less diluted cultures gave fewer viable cells compared to those obtained on plates spread with more diluted cultures. This unpredictability of growth on agar plate medium can be explained on the basis that the less diluted cultures contained higher numbers of viable cells which could produce larger concentrations of organic acids. These acids, in turn, reduced the pH of the medium to a greater extent and inhibited the growth of a large number of cells. In contrast, the growth on agar plates spread with more diluted culture containing a reduced number of viable cells, produced smaller concentrations of acids and hence, inhibitied relatively fewer cells. Thus more viable cell counts were observed in the latter case than in the former case.

This problem was overcome by adding glycerol and/or pyruvate as carbon substrate(s) in the growth medium. Both glycerol and pyruvate are non-fermentable carbon substrates and hence, the anaerobic pathways will not function during growth on these substrates. Therefore, only smaller concentrations of acids are produced during growth on these substrates (Table 5). As a result, the pH of the medium is not affected significantly and hence, the viable cell counts obtained on these plates are reliable and in agreement with the respective dilutions of the culture spread on the plates.

Since the plating efficiency of the agar plate medium containing glycerol and/or pyruvate as carbon substrate(s) was high and the cell viability was not affected after many sub-streakings, this plate medium proved to be very suitable for the short term maintenance of these strains.

The minimum growth pH observed for these Bacillus strains was 6.1. This pH is not very different from 5.8, the pH value reported for many other neutrophilic thermophiles (Sundaram, T. K. (1986) General, Molecularand Applied Microbiology Ed. Brock, T. D. John Wiley and Sons. Inc.). Since the culture pH fell quickly to about pH 5.0 with in 3-4 hours during the growth on a fermentable carbon substrate, it is likely that the inconsistency of viable cell counts we have observed for our strains may also exist for other neutrophilic microorganisms during their growth on agar plate media containing fermentable carbon substrates. In this case the TGP agar plate medium is useful for the efficient production of viable cell counts and the short term maintenance of a wide range of thermophilic microorganisms, provided that they are able to grow on these carbon substrates.

SEQUENCE LIST

<160> NUMBER OF SEQ ID NOS: 2

<210> SEQ ID NO 1
<211> LENGTH: 26
<212> TYPE: DNA
<213> ORGANISM: H. aegyptius

<400> SEQUENCE: 1
tctagaggag gatttttatg aattta                    26

<210> SEQ ID NO 2
<211> LENGTH: 25
<212> TYPE: DNA
<213> ORGANISM: h. AEGYPTIUS

```
                         -continued

<400> SEQUENCE: 2
ggatcctttc gatatttata ttctg                                        25
```

What is claimed is:

1. A method of producing a recombinant thermophilic Bacillus sp comprising in vivo methylation in a host cell by a non-endogenous DNA methylase of a heterologous gene and introduction of that methylated heterologous gene into the Bacillus, wherein the Bacillus is capable of growth at a temperature greater than 60° C.

2. The method according to claim 1, wherein the Bacillus is a facultative anaerobe.

3. The method according to claim 1 wherein the Bacillus is selected from B. stearothermophilus, B. calvodex; B. caldotenax; B. thermoglucosidasius; B. coagulans; B. lichenformis; B. thermodenitrflcans and B. caldolyticus.

4. The method according to claim 1, wherein the Bacillus is sporulation deficient.

5. The method according to claim 1, wherein the host cell is E. coli.

6. The method according to claim 1, wherein the DNA methylase is a HaeIII methyltransferase.

7. The method according to claim 1 wherein a shuttle vector which is able to replicate in both the host cell and the Bacillus sp is used to transfer the heterologous acne from the host cell to the Bacillus.

8. The method according to claim 1 wherein the methylated heterologous gene is incorporated into the chromosome of the recombinant Bacillus sp.

9. The method according to claim 1, wherein the methylated heterologous gene is introduced into the Bacillus by electroporation.

10. A method according to claim 1 in which the introduced gene increases ethanol production.

11. The method according to claim 7, in which the shuttle vector comprises the methylated, heterologous gene.

12. A thermophilic Bacillus sp which has been transformed with a methylated heterologous gene, wherein the Bacillus is capable of growth at a temperature greater than 60° C.

13. A Bacillus sp according to claim 12 wherein the Bacillus is selected from B. stearothermophilus; B. caldotenax; B. caldotenax; B. thermoglucosidasius; B. coagulans; B. licheniformis; B. thermodenitrificans and B. caldolyticus.

14. A Bacillus sp according to claim 12 in which the Bacillus is sporulation deficient.

15. The plasmid pUBUC as illustrated in FIG. 1.

Figure 2:
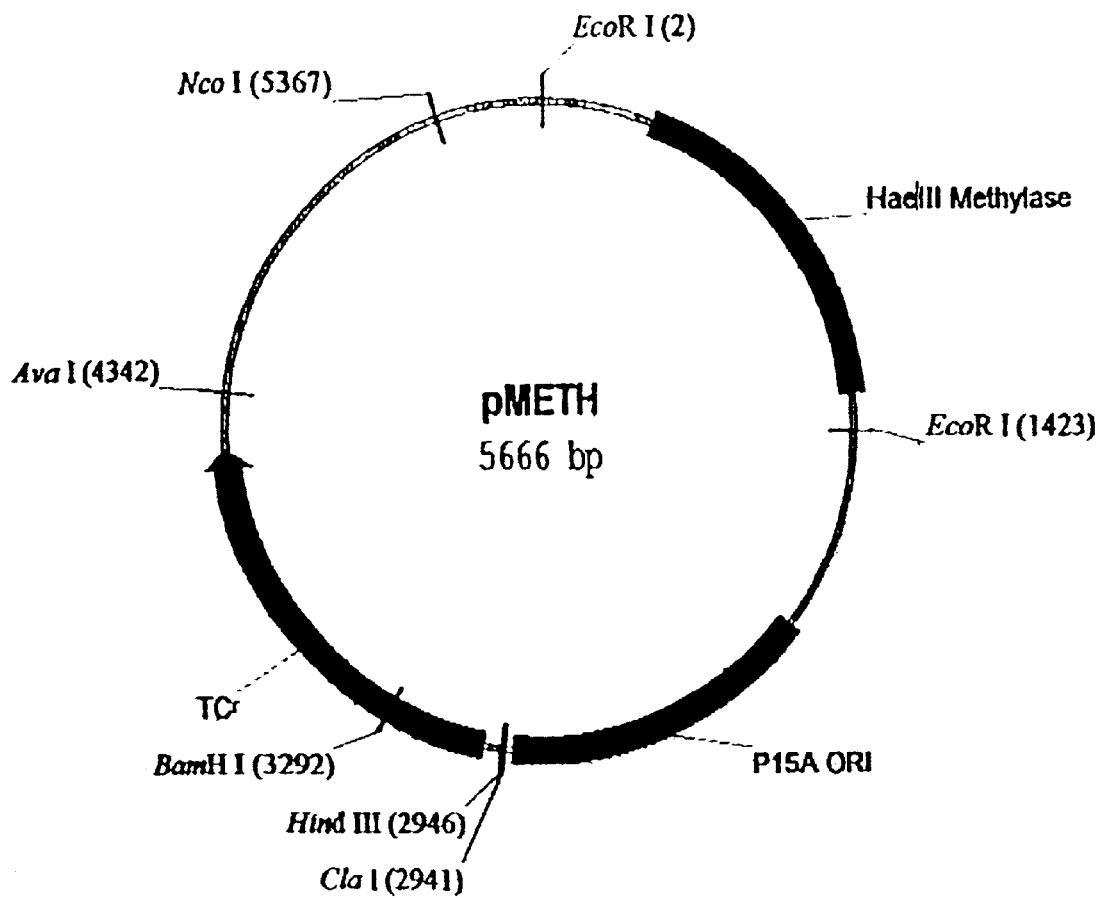
FIG. 2 is a schematic representation of plasmid pMETH.
Figure 2:
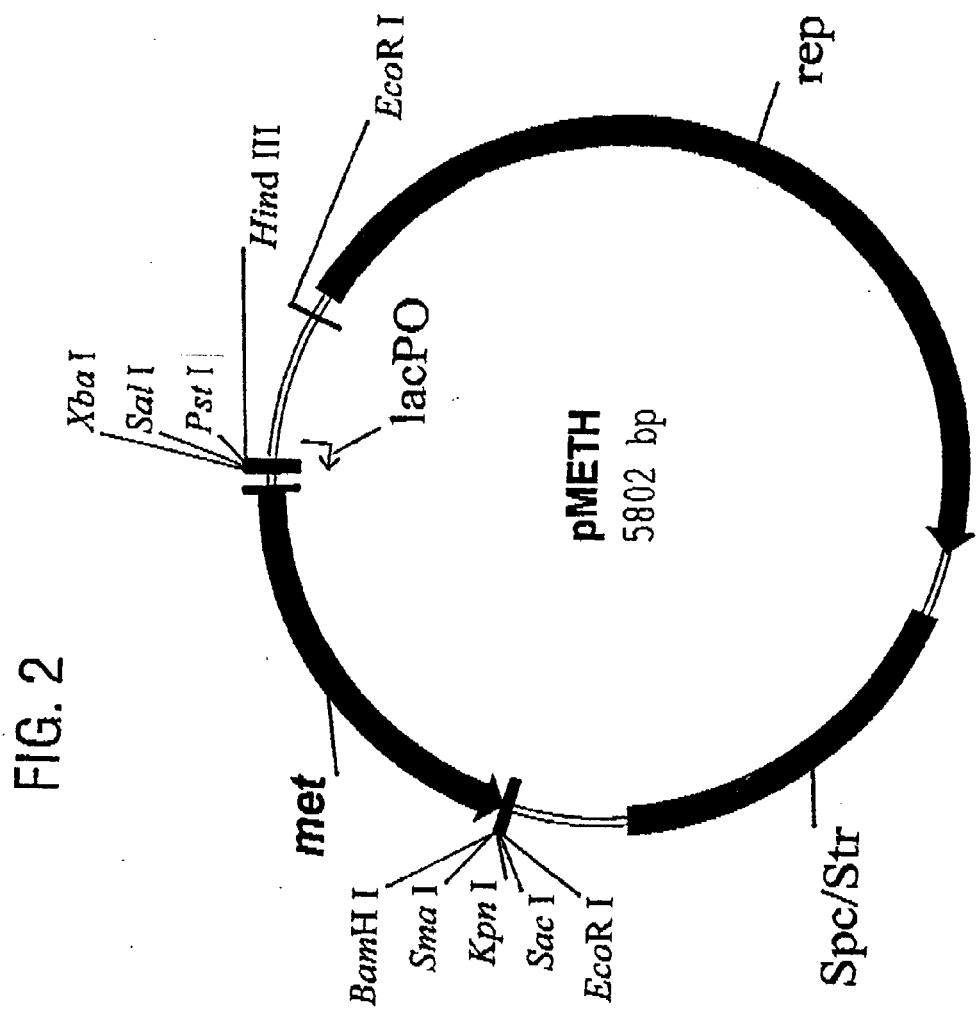

16. The plasmid pMETH as illustrated in FIG. 2.

* * * * *

UNITED STATES PATENT AND TRADEMARK OFFICE
CERTIFICATE OF CORRECTION

PATENT NO. : 6,664,076 B2
DATED : December 16, 2003
INVENTOR(S) : Edward M. Green et al.

It is certified that error appears in the above-identified patent and that said Letters Patent is hereby corrected as shown below:

Title page,
Item [30], Foreign Application Priority Data, please replace "0011186" with -- 0011186.4 --.

Drawings,
Sheet 2 of 3, please replace Figure 2 with the attached Figure.

Column 1,
Line 56, please replace "pyravate" with -- pyruvate --.

Column 5,
Line 43, please replace "PMETH" with -- pMETH --.

Column 8,
Line 9, please replace "Boebringer" with -- Boehringer --.
Line 13, please replace
"5'-TCTAGAGGAGGATTTTATGAATTTA-3'" with
--5'-TCTAGAGGAGGATTTTATGAATTTA-3'--.

Line 15, please replace
"5'-GGATCCTTTCGATATTATATTCTG-3'" with
--5'-GGATCCTTTCGATATTTATATTCTG-3'--.

Line 29, please replace "BamII1" with -- BamH1 --.

Column 17,
Line 20, please replace "*lichenformis*" with -- *licheniformis* -- and please replace "*thermodenitrflcans*" with -- *thermodenitrificans* --.
Line 29, please replace "acne" with -- gene --.

UNITED STATES PATENT AND TRADEMARK OFFICE
CERTIFICATE OF CORRECTION

PATENT NO.   : 6,664,076 B2
DATED        : December 16, 2003
INVENTOR(S)  : Edward M. Green et al.

It is certified that error appears in the above-identified patent and that said Letters Patent is hereby corrected as shown below:

Column 18,
Lines 23-24, please replace "*B. caldotenax*" with -- *B. calvodex* --.

Signed and Sealed this

Twenty-eighth Day of September, 2004

JON W. DUDAS
*Director of the United States Patent and Trademark Office*